US005696095A

United States Patent [19]
Piot et al.

[11] Patent Number: 5,696,095
[45] Date of Patent: Dec. 9, 1997

[54] PHARMACEUTICAL FORMULATIONS OF SPIRAMYCIN

[75] Inventors: Francois-Xavier Piot, Thiais; Robert Rona, Saint Germain En Laye, both of France

[73] Assignee: Rhone-Poulenc Rorer S.A., Antony Cedex, France

[21] Appl. No.: 470,319

[22] Filed: Jun. 6, 1995

Related U.S. Application Data

[63] Continuation-in-part of Ser. No. 411,620, Apr. 5, 1995, abandoned.

[51] Int. Cl.$^6$ ............................................. A61K 31/70
[52] U.S. Cl. ............................................. 514/30; 536/7.1
[58] Field of Search ................................. 514/30; 536/7.1

[56] References Cited

U.S. PATENT DOCUMENTS

| | | | |
|---|---|---|---|
| 4,375,468 | 3/1983 | Dunn | 424/230 |
| 5,082,653 | 1/1992 | Pan et al. | 424/53 |
| 5,403,594 | 4/1995 | Calvo et al. | 424/489 |

FOREIGN PATENT DOCUMENTS

| | | |
|---|---|---|
| 0 396 165 | 4/1990 | European Pat. Off. . |
| WO 92/09269 | 11/1991 | WIPO . |

OTHER PUBLICATIONS

Publ Citation/Patent Marcel Dekker, Inc. (New York), pp. 2–3, 96–99 (1986), Authors/Inventors or Assignee O'Brien Nabors Gelardi, Patent/Publ Title, Alternative Sweetners.

Publ Citation/Patent Chemical Abstracts, vol. 115, No. 115;57213u, p. 498 (1991), Authors/Inventors or Assignee Del Rio Alvarez, Calvo Matoe, Esteban Morales, Patent/Publ Title Water–dispersible spiramycin formulations.

*Primary Examiner*—Elli Peselev
*Attorney, Agent, or Firm*—Ross J. Oehler

[57] ABSTRACT

New formulations of spiramycin suitable for oral administration, particularly for children, comprise spiramycin and potassium acesulfame. These formulations mask the bitterness of spiramycin without adversely affecting the bioavailability or stability of the spiramycin. Preparation by wet granulation followed by dry state mixing is also disclosed.

5 Claims, No Drawings

PHARMACEUTICAL FORMULATIONS OF SPIRAMYCIN

CROSS-REFERENCE TO RELATED APPLICATION

This is a continuation-in-part (CIP) application of U.S. patent application Ser. No. 08/411,620 filed Apr. 5, 1995, now abandoned.

FIELD OF THE INVENTION

The present invention relates to new pharmaceutical formulations of spiramycin. It relates more particularly to new formulations intended to be administered orally.

BACKGROUND OF THE INVENTION

Spiramycin has been commercially available for nearly twenty-five years. However, spiramycin has proven very difficult to administer to man and, more particularly, to children in the form of a solution, suspension or dispersible granule because its bitterness is extremely difficult to mask.

Attempts to mask this bitterness include the formulation described in French published patent application number FR 2,669,533, which discloses spiramycin encapsulated by albumin by a technique which requires the use of organic solvents, such as isooctane, and their removal at the end of the process. This technique, although very efficient at taste-masking, is very expensive because it only allows the manufacture of small quantities of pharmaceutical composition and it necessitates stages of solvent recycling which are long and costly.

SUMMARY OF THE INVENTION

The present invention has made it possible to prepare spiramycin formulations having an enhanced taste without using solvent for its preparation. This enhanced taste masks the bitterness of spiramycin without adversely affecting bioavailability or stability of the spiramycin. The formulation comprises spiramycin and acesulfame, particularly potassium acesulfame.

The new pharmaceutical forms of spiramycin according to the present invention, which may also include flavoring agents, are intended to take the form of doses (sachets, bottles or packs with a measure, for example) containing a granulated powder to be dissolved or to be dispersed in water prior to administration to the patient.

This new granulated form, which can be suspended in water immediately before use, offers the following advantages:

ease of use during ambulatory treatment accuracy of the unit dosage easy suspension or dissolution in water easy absorption.

Numerous various formulation trials attempting to mask the bitterness have been undertaken. None of them gave satisfactory results as regards the taste of the aqueous suspension obtained or as regards the bioavailability of the spiramycin after absorption. However, the association between potassium acesulfame and spiramycin according to the present invention surprisingly has made it possible to achieve this objective.

DETAILED DESCRIPTION OF PREFERRED EMBODIMENTS

New granulated pharmaceutical forms of spiramycin for oral administration according to the present invention are prepared by wet granulation of the spiramycin and sucrose, preferably in a weight ratio of about 1/1 to about 1/9, followed by preparing in a dry state a mixture of the granules previously obtained, acesulfame, flavorings and any remaining sucrose.

The new formulations according to the invention preferably comprise about 100,000 to about 5,000,000 IU spiramycin, about 10 to about 20 mg potassium acesulfame, about 20 to about 200 mg flavorings and about qs 1 to about 10 g sucrose. According to one preferred embodiment, such formulations comprise 375,000 IU spiramycin, about 10 to about 20 mg potassium acesulfame, 60 mg flavorings and about qs 3 g sucrose. These formulations are preferred. One of ordinary skill in the art will appreciate that the formulations of the present invention may be adapted according to the desired masking of the bitterness of the active ingredient by adding more or less potassium acesulfame. The flavorings may also be adapted to the taste and to the age of the child.

These formulations may be presented either in the form of doses as mentioned above or in the form of a solution or suspension prepared immediately before use.

The invention will be described more fully with the aid of the following examples, which should not be considered as limiting the invention.

COMPARATIVE EXAMPLE 1

| | |
|---|---|
| spiramycin | 86.190 mg (375,000 IU) |
| Eudragit E 100 ® | 70.00 mg |
| mannitol qs | 950.00 mg |
| sodium saccharinate | 25.00 mg |
| strawberry flavoring | 40.00 mg |
| anhydrous colloidal silica | 12.50 mg |
| cellulose (microcrystalline) | 25.00 mg |
| polyvidone | 100.00 mg |
| sucrose | 97.50 mg |
| | 1250.00 mg |

Trials with this type of formula were stopped, in spite of the success of the taste masking, because of poor bioavailability.

COMPARATIVE EXAMPLE 2

Development of a simple and rational formula by preparation of a granule (concentrated) composed of sugar and spiramycin; and flavoring of the primary granule by the addition, in an external phase, of sweeteners and flavorings simply by mixing.

The manufacture of the primary granule is performed in a Turbosphere mixer-granulator-drier and the preparation of the final mixture in a gravity mixer.

Theoretical unit formula:

| | | |
|---|---|---|
| spiramycin base | 81.156 mg (375,000 IU) | |
| sucrose qs | 1000.00 mg | |
| sucrose (Alveo sugar) | 1960.00 mg | } external |
| banana flavoring | 40.00 mg | } phase |
| | 3000.00 mg | |

A bioavailability study demonstrated the bioequivalence of the granule of comparative trial 2 and of commercial syrup; however, the taste acceptability tests showed that the flavoring of the product requires improvements.

COMPARATIVE EXAMPLES 3 AND 4

The sweeteners commonly used (sodium saccharinate, sodium cyclamate) could not be selected because of the insufficient organoleptic effects.

An acceptability test was carried out on two of these formulations (one with sodium saccharinate (Example 4) and one with aspartame (Example 3)). The general formulations and results are indicated in Table 1 below. For aspartame, the taste acceptability test is satisfactory but the product interacts with spiramycin, thereby making its use impossible.

COMPARATIVE EXAMPLE 5

An attempt to mask the bitterness of spiramycin by association with xanthan gum. The general formulation is shown in Table 1. Results of taste testing were inconclusive but low.

EXAMPLE 6

The manufacture of sachets is carried out in 3 phases:

(a) Preparation of a concentrated primary granule (165 mg per sachet of 3 g containing 375,000 IU of spiramycin) in a Moritz mixer-granulator-drier:

| per sachet of 3 g | |
|---|---|
| spiramycin base | 84.081 mg (375,000 IU) |
| sucrose (superfine sugar) | qs 165.00 mg |
| water | about 5% by mass |

During the granulation, the product is heated with the aid of a jacket up to about 55° C. The stirring is carried out at about 100 revolutions/minute for 30 minutes. For the drying, the stirring is carried out at about 20 revolutions/minute while the temperature is maintained but while the pressure is reduced to between 6 and 20 KPa for 60 minutes.

The product is then cooled to room temperature over about 30 minutes.

The granule is sieved on a screen with a mesh of 0.71 mm.

(b) Preparation of the final granule in a cubic gravity mixer

| | |
|---|---|
| primary granule | 165.00 mg |
| potassium acesulfame | 10.00 mg |
| powdered strawberry flavoring | 30.00 mg |
| powdered raspberry flavoring | 30.00 mg |
| sucrose* qs | 3000.00 mg |

*superfine sugar and Alveo-sugar in a 1/1 ratio approximately.

(c) Distribution of the final mixture in an amount of:

3 g for the 375,000 IU dosage 6 g for the 750,000 IU dosage 12 g for the 1,500,000 IU dosage per sachet of paper/aluminum/polyethylene complex.

EXAMPLE 7

The procedures of Example 6 are repeated using qs 1 g sucrose in phase (a) per sachet of 3 g and 20 mg potassium acesulfame in phase (b).

The preparations described above (Examples 2-7) were submitted to taste testing and rated on a scale of 1 to 20 where 20 was the highest score. The results are set forth in Table 1.

TABLE 1

| | COMPARATIVE EXAMPLES 2 TO 5 | | | | INVENTION | |
|---|---|---|---|---|---|---|
| | $C_5$ | $C_2$ | $C_4$ | $C_3$ | 7 | 6 |
| spiramycin (IU) | 375,000 | 375,000 | 375,000 | 375,000 | 375,000 | 375,000 |
| sucrose | | qs 1 g | | qs 1 g | qs 1 g | qs 165 mg |
| starch | 3.5 mg | | | | | |
| xanthan gum | 15 mg | | | | | |
| PVP | | | 100 mg | | | |
| K acesulfame | | | | | 20 mg | 10 mg |
| aspartame | | | | 10 mg | | |
| saccharinate | | | 25 mg | | | |
| Eudragit E® | | | 70 mg | | | |
| mannitol | | | | 800 mg | | |
| flavorings | 20 mg | 40 mg | 40 mg | 20 mg | 60 mg | 60 mg |
| sucrose | qs 2.5 g | qs 3 g | qs 1.25 | qs 3 g | qs 3 g | qs 3 g |
| score out of 20 | 6.25 | poor | 14 | non-bio equivalent | 15 | acceptable |
| remarks | | | | interaction between spiramycin and aspartame | | |

The formulations according to the present invention (Examples 6 and 7) show a marked improvement compared with the prior art formulations regarding masking of the taste and aftertaste of spiramycin.

The present invention may be embodied in other specific forms without departing from the spirit or essential attributes thereof and, accordingly, reference should be made to the appended claims, rather than the specification, as indicating the scope of the invention.

We claim:

1. A spiramycin formulation for paroral administration comprising spiramycin and potassium acesulfame.

2. The formulation according to claim 1, wherein the formulation is provided in granulated form for suspension or dissolution in water.

3. The formulation according to 1, comprising about 100,000 to about 5,000,000 IU spiramycin, about 10 to about 20 mg potassium acesulfame, about 10 to about 200 mg flavoring and about qs 1 to about 10 g sucrose.

4. The formulation according to claim 3, comprising 375,000 IU spiramycin, about 10 to about 20 mg potassium acesulfame, 60 mg flavoring and qs 3 g sucrose.

5. A process for preparing the spiramycin formulation according to claim 3, comprising the steps of wet granulating the spiramycin and at least a portion of the sucrose to obtain spiramycin granules, and mixing, in a dry state, the granules, the acesulfame, the flavoring and any remaining sucrose.

* * * * *